United States Patent [19]

Musha

[11] Patent Number: 4,799,796
[45] Date of Patent: Jan. 24, 1989

[54] METHOD AND APPARATUS FOR MEASURING IMMUNOLOGICAL REACTION WITH THE AID OF PHASE-MODULATION OF LIGHT

[75] Inventor: Toshimitsu Musha, Machida, Japan

[73] Assignee: Olympus Optical Company, Ltd., Tokyo, Japan

[21] Appl. No.: 941,107

[22] Filed: Dec. 12, 1986

[30] Foreign Application Priority Data

Dec. 20, 1985 [JP] Japan .............................. 60-285819

[51] Int. Cl.⁴ .................... G01N 33/50; G01N 21/21; G01N 21/51; G01N 15/02
[52] U.S. Cl. ................................. 356/336; 356/351; 356/364
[58] Field of Search ............... 356/351, 336, 337, 338, 356/364, 365, 366, 367, 368

[56] References Cited

U.S. PATENT DOCUMENTS

| | | | |
|---|---|---|---|
| 4,233,664 | 11/1980 | Grandchamp | 356/336 |
| 4,480,916 | 11/1984 | Bareket et al. | 356/351 |
| 4,725,140 | 2/1988 | Musha | 356/336 |

Primary Examiner—Richard A. Rosenberger
Attorney, Agent, or Firm—Parkhurst, Oliff & Berridge

[57] ABSTRACT

In order to measure the antigen-antibody reaction, a linearly polarized laser light beam is divided into first and second light beams and the first light beam is made incident upon a cell containing a reaction liquid including particles. The second light beam is phase-modulated by an optical phase-modulator with a phase-modulating angular frequency $\omega^0$. A phase-modulated light beam emanating from the phase-modulator is made incident upon a photodetector together with light scattered by agglutinated particles via an analyzer having a polarization plane perpendicular to that of the linearly polarized light beam. An output signal of the photodetector is synchronously detected with a reference signal having a frequency of $m\omega_0/2\pi$, where m is a natural number.

24 Claims, 2 Drawing Sheets

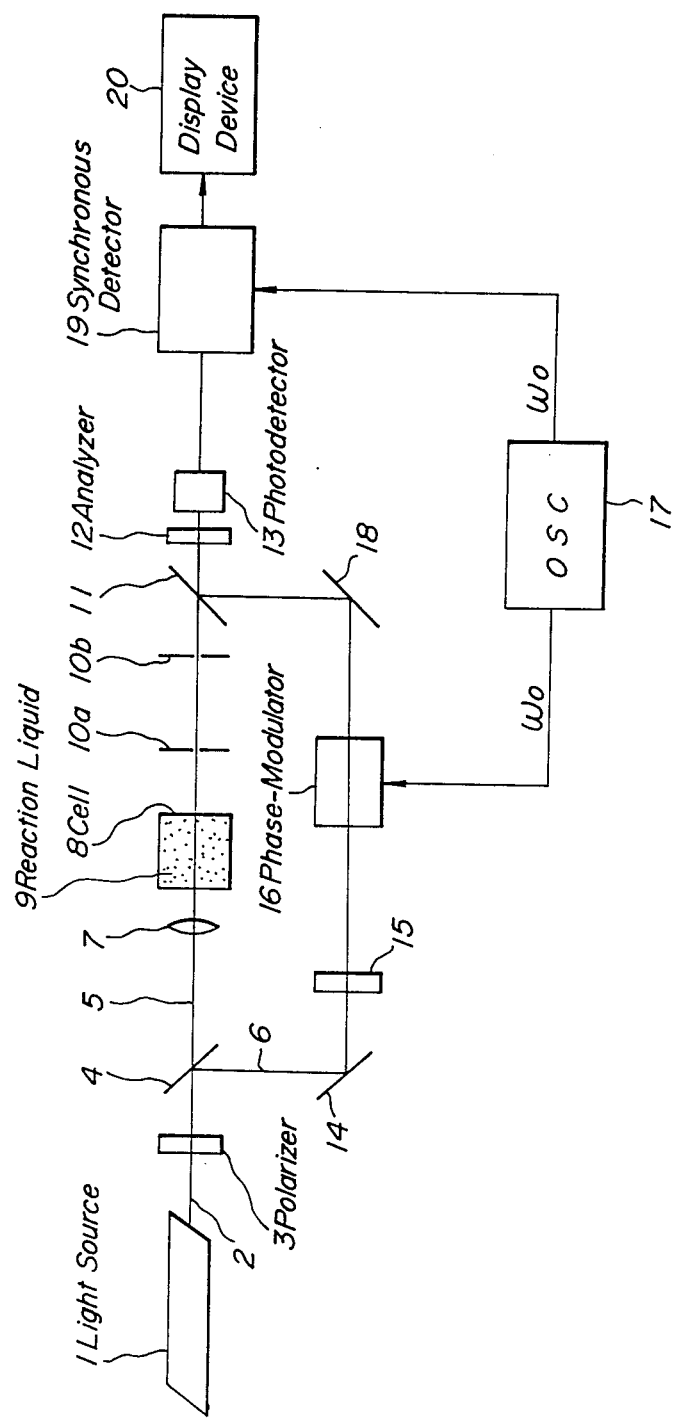

FIG_2A
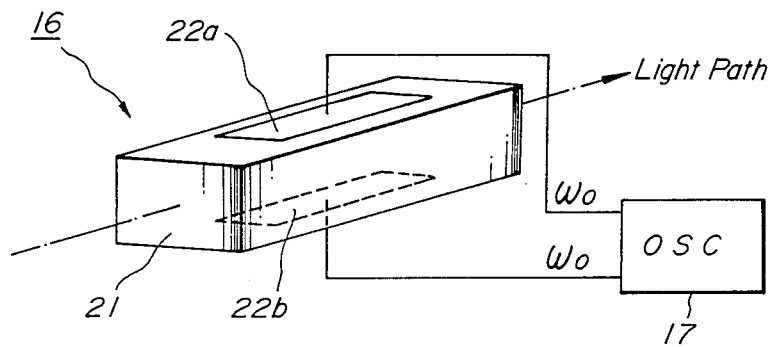
FIG_2B
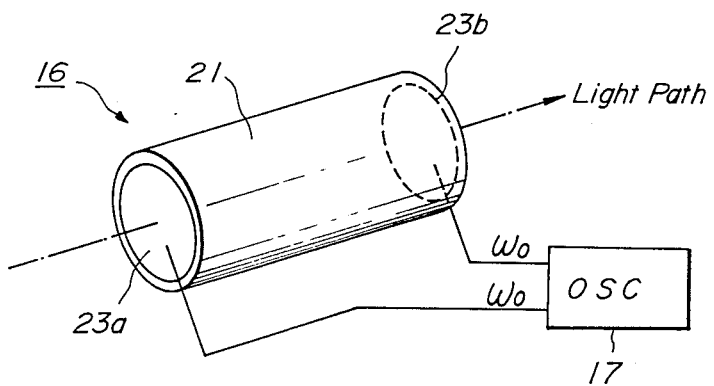

METHOD AND APPARATUS FOR MEASURING IMMUNOLOGICAL REACTION WITH THE AID OF PHASE-MODULATION OF LIGHT

BACKGROUND OF THE INVENTION

Field of the Invention and Related Art Statements

The present invention relates to method and apparatus for measuring an immunological antigen-antibody reaction with the aid of phase information of polarized light scattered by fine particles suspended in a reaction liquid.

There has been developed an immunological analysis for measuring immune substances, hormones, medicines, and various components such as immune regulators faintly contained in living bodies by utilizing specific immunological reactions. The immunological analysis may be roughly classified into a labeling immunological analysis in which enzymes and isotopes are used as an indicator substance, and a non-labeling immunological analysis in which antigen-antibody complexes are directly measured.

In the former labeling immunological analysis, there have been widely known radio immuno assay (RIA), enzyme immuno assay (EIA) and fluorescent immuno assay (FIA). These assays have an advantage that a high sensitivity can be attained, but also have a drawback that handling of isotopes and wasted liquid is difficult, measuring periods are long and labeling reagents are expensive so that the test cost per sample, i.e. running cost, is liable to be high.

In non-labeling immunological analysis, there have been developed immuno electrophoresis, immuno diffusion and sedimentation. These methods are rather simple, but do not have sufficiently high sensitivity, quantitativeness and reproducibility necessary for precise measurement.

In "Immuno chemistry", vol. 12, No. 4 (1975) pages 349 to 351, there has been proposed an immunological analysis in which an antigen or antibody bound on surfaces of fine particles are reacted with an antibody or antigen contained in a test liquid, and average diffusion constant which is an indicia of the Brownian motion of aggregates composed of agglutinated particles is measured from a variation in a spectral width of laser light scattered from a solution of particles. This method has a merit that no reagent is depleted. However, since the spread of the spectrum due to the Doppler effect owing to the Brownian motion of aggregates is detected by a spectrometer, the apparatus is liable to be large in size and expensive in cost. Further, error might be induced when the spectrometer is driven mechanically, so that precision and reproducibility become worse. Moreover, in this known method, because the average diffusion constant is measured from the spectral width, the amount of available information about the antigen-antibody reaction is limited.

In order to avoid the above mentioned drawbacks, the inventor of the present invention has conducted various experiments and analyses and proposed a novel method of measuring the immunological reaction by detecting a fluctuation in intensity of light scattered by particles. Such a method has been disclosed in U.S. patent application Ser. No. 754,272 filed on July 12, 1985.

After developing such a method, the inventor has further conducted various experiments and has designed an improved method in which linearly polarized light is made incident upon a reaction liquid via a polarizer and light scattered by particles is detected through an analyzer which has a polarization plane perpendicular to that of the polarizer. This method is based on the fact that when the linearly polarized light is scattered by the particles, the polarization condition of the scattered light has an intimate relation with the antigen-antibody reaction.

The inventor has experimentally confirmed that the above method has the following drawbacks. In order to improve the measuring sensitivity when a concentration of particles is increased, there occurs multiple scattering and this results in the scattered light containing a polarization component perpendicular to the polarization plane of the incident linearly polarized light although the antigen-antibody reaction does not take place in the cell, so that the sensitivity might be decreased and the immunological reaction can not be measured accurately.

SUMMARY OF THE INVENTION

The present invention has for its object to provide a method and an apparatus for measuring an immunological reaction, in which the measuring sensitivity can be increased without affecting the measuring accuracy and reliability, while the measurement can be performed within a short time period in an automatic manner without using expensive reagents and an expensive and large spectrometer.

According to the invention a method of measuring an immunological reaction comprises emitting a polarized light beam;

dividing the polarized light beam into first and second polarized light beams;

projecting the first polarized light beam to a reaction liquid containing at least antigen and antibody;

phase-modulating said second polarized light beam with a given phase-modulating angular frequency to produce a phase-modulated light beam;

introducing said phase-modulated light beam and light scattered by particulate substances in the reaction liquid and having polarization component whose polarization plane differs from that of the first polarized light beam, onto a photodetector to produce an output signal; and processing said output signal of the photodetector on the basis of said phase-modulating angular frequency to measure the antigen-antibody reaction in the reaction liquid.

According to the invention an apparatus for measuring an antigen-antibody reaction by projecting polarized light to a reaction liquid containing at least antigen and antibody and by detecting light scattered by particulate substances in the reaction liquid, comprises a light source means for emitting a polarized light beam;

a cell means for containing an antigen-antibody reaction liquid;

a beam splitting means for dividing said polarized light beam into first and second polarized light beams;

a means for projecting said first polarized light beam to said cell;

a phase-modulating means for phase-modulating said second polarized light beam with a given phase-modulating angular frequency $\omega_0$ to generate a phase-modulated light beam;

an analyzer means having a polarization plane which is different from that of the polarized light beam;

a means for directing light scattered by particulate substances in the reaction liquid into said analyzer means;

a photodetector means for receiving a light beam emanating from said analyzer means and said phase-modulated light beam to produce an output signal; and a signal processing means for processing said output signal of the photodetector means on the basis of said phase-modulating angular frequency to measure the antigen-antibody reaction in the reaction liquid.

When linearly polarized light is made incident upon a cell containing a reaction liquid, the light is scattered by fine particles in the reaction liquid and a condition of polarization of the scattered light varies in accordance with a condition of agglutination of particles. Particles which are not agglutinated with each other have a spherical shape and therefore the light scattered forwardly by the round particles is linearly polarized in the same polarization plane as the incident linearly polarized light as long as the diameter d of particle is sufficiently smaller than a wavelength $\lambda$ of light ($d < \lambda$). When the antigen-antibody reaction occurs and particles are bound with each other, agglutinated particles could not have a spherical shape and have an optical antisotropy. Therefore, the light scattered by such agglutinated particles has polarization components which are different from the polarization plane of the incident light, and further the phase of the scattered light does not fluctuate. Therefore, if it is assumed that only a single forward scattering occurs, i.e. the incident light is scattered only once, only the light scattered by the agglutinated particles can be selectively detected by receiving the scattered light via an analyzer having the polarization plane different from that of the incident light. In such a case, an output of a photodetector varies in accordance with the agglutinated condition of particles, i.e. the degree of the antigen-antibody reaction, so that the immunological reaction can be measured by processing the output signal of the photodetector.

However, in order to increase the sensitivity of the measurement, it is necessary to make higher the concentration of particles contained in the reaction liquid. Then the light is scattered multiple times by particles. In such a multiple scattering, the phase of the scattered light might vary at random even if the particles have the spherical shape and light is scattered forwardly, i.e. the agglutinating reaction does not occur. Therefore, even by detecting the scattered light via the analyzer, the multiple scattered light due to non-agglutinated particles might be made incident upon the photodetector. In this manner, it is practically impossible to effect the measurement accurately.

The present invention has been done on the basis of the fact that the phase of light scattered multiple times by non-agglutinated particles varies at random. According to the invention a part of the incident light is separated and phase-modulated, and phase-modulated light is made incident upon the photodetector together with the scattered light emanating from the cell. The output signal of the photodetector is processed in accordance with a phase-modulation angular frequency of the phase-modulated light. Then, it is possible to detect selectively a light component scattered by agglutinated particles only once, said light component having a coherent phase with the incident light.

An electric field E of light incident upon a light receiving surface of the photodetector can be expressed as follows.

$$E = E_1\cos[\omega t + \phi_1] + E_2\cos[\omega t + \phi_2(t)]E_3\cos[\omega t + a\cos\omega_0 t + \phi_3] \quad (1)$$

In this equation (1), $E_1\cos[\omega t + \phi_1]$ represents an intensity of the electric field of light scattered by agglutinated particles once, and $\phi_1$ is a phase constant. The second term $E_2\cos[\omega t + \phi_2(t)]$ represents an intensity of the electric field of light scattered by non-agglutinated particles by multiple times, and $\phi_2(t)$ denotes random phase constant. The third term $E_3\cos[\omega t + a\cos\omega_0 t + \phi_3]$ represents an intensity of electric field of incident light phase-modulated by $a\cos\omega_0 t$, where $\omega_0$ is a phase-modulating angular frequency. $\phi_1$ denote phase constant which is generally different from $\phi_3$.

In general, an output signal $E^2$ of the photodetector having a square-low detection characteristic may be expressed in the following manner.

$$E^2 = \overline{\{E_1\cos[\omega t + \Phi_1] + E_2\cos[\omega t + \Phi_2(t)] + E_3\cos[\omega t + a\cos\omega_0 t + \Phi_3]\}^2} = \tfrac{1}{2}E_1^2 + \tfrac{1}{2}E_2^2 + \tfrac{1}{2}E_3^2 + $$

$$E_1 E_2 \overline{(\cos[\omega t + \Phi_1])(\cos\{\omega t + \Phi_2(t)\})} +$$

$$E_1 E_3 \overline{(\cos[\omega t + \Phi_1])(\cos[\omega t + a\cos\omega_0 t + \Phi_3])} +$$

$$E_2 E_3 \overline{(\cos[\omega t + \Phi_2(t)])(\cos[\omega t + a\cos\omega_0 t + \Phi_3])} \quad (2)$$

In the above equation (2), only a fifth term has a component which varies at an angular frequency $n\omega_0$ (n is a natural number), because both the fourth and sixth terms have random components of $\cos\phi_2(t)$ and $\sin\phi_2(t)$ and their averages become zero. The fifth term may be rewritten as follows by using the Bessel function.

$$\overline{E_1 E_3 (\cos[\omega t + \Phi_1])(\cos[\omega t + a\cos\omega_0 t + \Phi_3])} = E_1 E_3 \tfrac{1}{2}(\cos[\omega t + \Phi_1 + \Phi_3] + \cos[\Phi_1 - \Phi_3])\left\{ J_0(a) + \sum_{n=1}^{\infty} 2(-1)^n J_{2n}(a)\cos 2n\omega_0 t \right\} - $$

$$E_1 E_3 \tfrac{1}{2}(\sin[2\omega t + \Phi_1 + \Phi_3] - \sin[\Phi_1 - \Phi_3])\left\{ \sum_{n=1}^{\infty} 2(-1)^{n+1} J_{2n-1}(a)\cos[(2n-1)\omega_0 t] \right\} \quad (3)$$

In the above equation (3), an amplitude of a component which varies at an angular frequency $(2n-1)\omega_0$ may be expressed as follows.

$$E_1 E_3 \sin(\phi_1 - \phi_3) J_{2n-1}(a) \quad (4)$$

Further, an amplitude of a component which varies at an angular frequency $2n\omega_0$ may be represented by the following equation.

$$E_1 E_3 \cos(\phi_1 - \phi_3) J_{2n}(a) \quad (5)$$

Therefore, when only components of the output signal of the photodetector which vary at angular frequencies $\phi_0$, $2\omega_0$, $3\omega_0$, $4\omega_0$ ..., i.e. $m\omega_0$ (m is a natural number) are selectively detected, it is possible to detect the light scattered by agglutinated particles only once. Due to characteristics of the Bessel function, by selecting m=1 and a=2, it is possible to attain the maximum output.

BRIEF DESCRIPTION OF THE DRAWINGS

FIG. 1 is a schematic view showing an embodiment of the immunological reaction measuring apparatus according to the invention; and FIGS. 2A and 2B are perspective views illustrating two embodiments of the phase-modulator shown in FIG. 1.

DESCRIPTION OF THE PREFERRED EMBODIMENTS

FIG. 1 is a schematic view showing an embodiment of the immunological reaction measuring apparatus according to the invention. In the present embodiment, a light source for emitting coherent light is constructed by He-Ne gas laser 1 emitting a laser beam having a wavelength of 632.8 nm. The light source emitting the coherent light may be formed by a solid state laser such as a semiconductor laser. A laser light flux 2 emitted from the light source 1 is passed through a polarizer 3 which may be formed by a Glan-Thompson prism and then is divided by a half mirror 4 into light fluxes 5 and 6. The light flux 5 is collected by a condenser lens 7 and is made incident upon a cell 8. The cell 8 is made of transparent quartz.

In the cell 8 is contained an antigen-antibody reaction test liquid 9 which is a mixture of a buffer solution in which fine spherical particles such as polystyrene latex particles and a test sample containing antigen or antibody to be tested are suspended. On outer surfaces of particles is bound an antibody or antigen such as immuno-globulin G (IgG) which is specifically reacted with the antigen or antibody in the test sample. Therefore, in the cell 8, the antigen-antibody reaction occurs and attractive forces are generated between particles. Then the particles are agglutinated with each other to form aggregates and the polarization condition of scattered light is changed in accordance with the size and shape of the aggregates.

The light scattered by particles in the cell 8 is passed through a collimator including a pair of slits 10a, 10b, a half mirror 11 and an analyzer 12 and then is made incident upon a photodetector 13 constructed by a photomultiplier tube having a very high sensitivity. The analyzer 12 has a polarization plane which is perpendicular to that of the polarizer 3. In the present embodiment, the photodetector 13 receives the light flux scattered from the cell toward the same direction as the direction of the incident light beam 5.

The light flux 6 divided by the half mirror 4 is reflected by a reflection mirror 14 and is passed through a half-wavelength plate 15 to rotate its polarization plane by 90° so that the polarization plane of the light emanating from the half-wavelength plate 15 is made identical with that of the analyzer 12. The light emanating from the half-wavelength plate 15 is made incident upon a phase-modulator 16 and is phase-modulated with a modulating signal having an angular frequency $\omega_0$ supplied from an oscillator 17, so that a linearly polarized light having a phase which varies in accordance with $\cos[\omega t + a\cos\omega_0 t + \phi_3]$ is obtained. The thus phase-modulated light is made incident upon the photodetector 13 by means of a reflection mirror 18, the half-mirror 11 and the analyzer 12.

An output signal of the photodetector 13 is supplied to a synchronous detector 19 which effects the synchronous detection with the aid of a reference signal of frequency $\omega_0/2\pi$ supplied from the oscillator 17. An output signal of the synchronous detector 19 is supplied to a display device 20 and is displayed thereon. In the present embodiment, the output signal of the photodetector 13 is synchronously detected at the frequency of $\omega_0/2\pi$. The frequency $\omega_0/2\pi$ may be set to a frequency such as 2 KHz which is higher than the Doppler frequency. A modulation index a of the phase-modulator 16 is preferably so determined that the equations (4) and (5) can assume the maximum values so as to attain the maximum sensitivity. This means that a=2.

As explained above, according to the invention the output signal of the synchronous detector 19 depends solely on the light scattered by agglutinated particles only once and thus on the concentration of the antigen or antibody contained in the sample. Therefore, by previously deriving a calibration curve by using standard samples having known concentrations, it is possible to measure an unknown concentration of a sample from the output signal of the synchronous detector 19. Further, as can be read from the equations (4) and (5), the output signal of the photodetector 13 can be represented by a product of $E_1$ and $E_3$, and it is possible to increase the gain of the output signal of the synchronous detector by increasing $E_3$. Moreover, since the influence of the multiple scattering due to non-agglutinated particles can be avoided, it is possible to carry out the measurement at a high sensitivity by increasing the number of particles contained in the reaction liquid.

FIGS. 2A and 2B illustrate two embodiments of the phase-modulator 16 shown in FIG. 1. The phase-modulator 16 utilizes the Pockels effect and the phase of light transmitted through a crystalline substance is modulated by applying an electric field to the crystalline substance. In the embodiment shown in FIG. 2A, a pair of electrodes 22a and 22b are provided on opposite sides of light path formed in a crystalline optical member 21, and an electric field is generated across the electrodes by applying to the electrodes a signal of angular frequency $\omega_0$ from the oscillator 17. In the embodiment depicted in FIG. 2B, a pair of transparent electrodes 23a and 23b are applied on entrance and exit surfaces of a crystalline optical member 21 and an electric field is generated across the electrodes.

The present invention is not limited to the embodiments mentioned above, but may be modified in various manner. In the above embodiment, immuno globulin G (IgG) is used as the antigen to be tested, but any other substances such as immuno globulin A (IgA), IgM, IgD, IgE, Australia antigen, and insurine which cause agglutination by the antigen-antibody reaction. Further, in the above embodiments, antibody is bound on the particle surface and antigen in a test sample is measured, but antibody in a test sample may be detected by using particles having antigen bounded thereon. In the above embodiments, use is made of polystyrene latex particles, but any other organic particles and inorganic particles such as glass beads may be used. Moreover, in the above embodiments, particles are existent in the test solution before the reaction, but it is also possible to utilize particulate substances which are produced by the antigen-antibody reaction. For instance, when human villus gonadotropin (HCG) is used as the antigen and anti-human villus gonadotropin (anti-HCG) is used as the antibody, then the antigen-antibody complex produced by the antigen-antibody reaction can be used as particles. Further, the antigen itself may be used as particle. An example of such an antigen-antibody reaction is a reaction in which candida albicans (yeast) is used as the antigen and anti-candida albicans is used as the antibody. Moreover, blood corpuscles, cells and microorganisms may be used as particles. Further in the embodiment shown in FIG. 1, the measurement is carried out by the batch system in which test solutions are successively poured into the cell, but use may be made of a flow system in which antigen-antibody reaction liquid is continuously flowed through the cell. It should be further noted that in the embodiments so far explained the light source is formed by the laser light source emitting coherent light, but any light source emitting incoherent light may be also used. Further, according to the invention, use may be made of light other than linearly polarized light such as circularly polarized light and elliptically polarized light.

In the above embodiment, the signal component of the output of the photodetector having the phase-modulating angular frequency $\omega_0$ is detected by the synchronous detector. It is also possible to derive simultaneously frequency components having frequencies $\omega_0/2\pi$ and $2\omega_0/2\pi$ by using two synchronous detectors to which are supplied reference signals having the frequencies of $\omega_0/2\pi$ and $2\omega_0/2\pi$, respectively. Moreover, any desired frequency component may be derived by using a band pass filter having a transmission band with a center frequency of $\omega_0/2\pi$, $2\omega_0/2\pi$ . . . or $m\omega_0/2\pi$. In this case, it is preferable to use a comb filter having a plurality of transmission bands with center frequencies of $\omega_0/2\pi$, $2\omega_0/2\pi$ . . . and $m\omega_0/2\pi$.

Moreover, in the embodiment explained above, in order to prevent light once scattered by non-agglutinated particles and a part of the incident light which is not reflected by particles from being made incident upon the photodetector, the analyzer is arranged in front of the photodetector. However, it is not necessary to make incident the phase-modulated light incident upon the photodetector through the analyzer, and thus the analyzer may be arranged in front of the half mirror 11. Then, the phase-modulated light will be directly made incident upon the photodetector. In such a case, the setting of the optical phase-modulator may not necessarily be strict. Even in such a case, the half-wavelength plate 15 may be advantageously placed in the reference light path.

As explained above in detail, according to the invention, the linearly polarized light is separated into two beams and one of the beams is made incident upon the reaction liquid and the other beam is phase-modulated by a modulation frequency $\omega_0$. The phase-modulated light beam and light scattered by particles contained in the reaction liquid are commonly made incident upon the photodetector, and the output signal of the photodetector is synchronously detected on the basis of the modulation frequency $\omega_0$. Therefore, the influence of light scattered multiple times by non-agglutinated particles by multiple times can be avoided or mitigated effectively. In this manner, the measurement can be performed accurately and reliably, and the measurement sensitivity can be improved by increasing the concentration of particles in the reaction liquid.

What is claimed is:

1. A method of measuring an immunological reaction comprising the steps of:
    emitting a polarized light beam;
    dividing the polarized light beam into first and second polarized light beams;
    projecting the first polarized light beam to a reaction liquid containing at least an antigen and an antibody;
    phase-modulating said second polarized light beam with a given phase-modulating angular frequency to produce a phase-modulated light beam;
    introducing said phase-modulated light beam and light scattered by particulate substances in the reaction liquid and having a polarization component whose polarization plane differs from that of the first polarized light beam, onto a photodetector to produce an output signal; and
    processing said output signal of the photodetector on the basis of said phase-modulating angular frequency to measure the antigen-antibody reaction in the reaction liquid.

2. A method according to claim 1, wherein said step of emitting the polarized light beam emits a linearly polarized light beam.

3. A method according to claim 2, wherein at least said light scattered by the particulate substances in the reaction liquid is made incident upon said photodetector by means of an analyzer whose polarization plane is perpendicular to that of the linearly polarized light beam.

4. A method according to claim 3, wherein a polarization plane of said phase-modulated light beam is rotated by 90° with respect to a polarization plane of said second polarized light beam, and the phase-modulated light beam is made incident upon the photodetector through said analyzer.

5. A method according to claim 4, wherein said second polarized light beam is made incident upon a phase-modulator by means of a half-wavelength plate.

6. A method according to claim 1, wherein the output signal of the photodetector is processed by a synchronous detector to which is supplied a reference signal having a frequency of $m\omega_0/2\pi$, wherein $\omega_0$ is the phase-modulating angular frequency and m is a natural number.

7. A method according to claim 6, wherein m is set to 1.

8. A method according to claim 7, wherein said second polarized light beam is phase-modulated with a modulation index a equal to 2.

9. A method according to claim 1, wherein said output signal of the photodetector is supplied to a band pass filter having at least one transmission band with a center frequency $m\omega_0/2\pi$, wherein $\omega_0$ is the phase-modulating angular frequency and m is a natural number.

10. A method according to claim 1, wherein said particulate substances in the reaction liquid are formed by particles which are initially introduced in the reaction liquid and have an antigen or antibody bounded thereon.

11. A method according to claim 10, wherein said particles are made of polystyrene latex.

12. A method according to claim 1, wherein said particulate substances are formed by particulate productions produced by the antigen-antibody reaction.

13. A method according to claim 1, wherein said light introduced into the photodetector is formed by light scattered in a direction in which said first polarized light beam is made incident upon the reaction liquid.

14. An apparatus for measuring an antigen-antibody reaction by projecting polarized light to a reaction liquid containing at least an antigen and an antibody and by detecting light scattered by particulate substances in the reaction liquid, comprising
- a light source means for emitting a polarized light beam;
- a cell means for containing an antigen-antibody reaction liquid;
- a beam splitting means for dividing said polarized light beam into first and second polarized light beams;
- a means for projecting said first polarized light beam to said cell;
- a phase-modulating means for phase-modulating said second polarized light beam with a given phase-modulating angular frequency $\omega_0$ to generate a phase-modulated light beam;
- an analyzer means having a polarization phase which is different from that of the polarized light beam;
- a means for directing light scattered by particulate substances in the reaction liquid into said analyzer means;
- a photodetector means for receiving a light beam emanating from said analyzer means and said phase-modulated light beam to produce an output signal; and
- a signal processing means for processing said output signal of the photodetector means on the basis of said phase-modulating angular frequency to measure the antigen-antibody reaction in the reaction liquid.

15. An apparatus according to claim 14, wherein said light source means comprises a laser light source emitting a coherent laser light beam and a polarizer arranged to transmit said coherent laser light beam as a linearly polarized light beam.

16. An apparatus according to claim 15, wherein the polarization plane of said polarizer is perpendicular to the polarization plane of the analyzer means.

17. An apparatus according to claim 16, further comprising a beam composing means for composing said light scattered by the particulate substances and said phase-modulated light beam with each other.

18. An apparatus according to claim 17, wherein said beam composing means is arranged between said cell means and said analyzer means.

19. An apparatus according to claim 18, further comprising an optical means for rotating the polarization plane of said second polarized light beam by 90°.

20. An apparatus according to claim 14, wherein said signal processing means comprises a synchronous detector for synchronously detecting said output signal of the photodetector in accordance with a reference signal having a frequency of $m\omega_0/2\pi$, wherein m is a natural number.

21. An apparatus according to claim 20, further comprising an oscillator for generating said reference signal, an output signal of said oscillator being supplied to said phase-modulating means as a modulating signal.

22. An apparatus according to claim 14, wherein said phase-modulating means comprises an optical member made of a crystalline substance for defining an optical path, and a pair of electrodes applied on said optical member.

23. An apparatus according to claim 22, wherein said pair of electrodes are arranged on respective sides of the optical path.

24. An apparatus according to claim 22, wherein said pair of electrodes are made of transparent material and are arranged at an entrance and an exit of the optical path.

* * * * *